United States Patent [19]

Said et al.

[11] Patent Number: 4,972,718
[45] Date of Patent: Nov. 27, 1990

[54] ASSESSMENT OF DAMAGE IN KERATIN FIBERS

[75] Inventors: Hayel M. Said, Simi Valley; Leroy D. Hunter, Thousand Oaks; Roger A. Mathews, Newbury Park, all of Calif.

[73] Assignee: Redken Laboratories Inc, Canoga Park, Calif.

[21] Appl. No.: 494,768

[22] Filed: Mar. 16, 1990

[51] Int. Cl.$^5$ .............................................. G01D 7/02
[52] U.S. Cl. ..................................................... 73/789
[58] Field of Search ................. 73/789, 794, 795, 826, 73/828, 160

[56] References Cited

U.S. PATENT DOCUMENTS 3,921,443 11/1975 Yates .
4,061,022 12/1977 Yates .
4,628,742 12/1986 Golding .
4,635,654 1/1987 Mathews et al. .................... 132/251

FOREIGN PATENT DOCUMENTS 0165035 9/1983 Japan ...................................... 73/794

OTHER PUBLICATIONS

Edman, et al., "Properties of Peroxide-Bleached Hair", J. Soc. Cosmet Chem, vol. 12(3); 133-145 (1961).

Jachowicz, "Hair Damage and Attempts to Its Repair", J. Soc. Cosmet. Chem., 38, 263-286 (July/Aug. 1987).
Wolfram, et al., "The Mechanism of Hair Bleaching", J. Soc. Cosmet Chem, 21, 875-900 (Dec. 9, 1970).
Robbins, "Physical Properties and Cosmetic Behavior of Hair", Springer, Verlag. 1988.

Primary Examiner—Robert Raevis
Attorney, Agent, or Firm—Christie, Parker & Hale

[57] ABSTRACT

The condition of hair or other keratin fibers can be evaluated by measuring the force required to obtain a first value of elongation of the fiber in the yield region of the force-elongation curve, and the force required to obtain a second value of elongation of the fiber in the yield region. The ratio of these two measured forces is then determined as a damage index for the fiber. It is found that a constant force ratio is obtained for wet virgin keratin fiber independent of fiber diameter or the source of the fiber. It is also found that the force ratio changes as a function of subjective or objective measures of chemical damage to the hair fiber. The force ratio or damage index can, therefore, be used for identifying hair care products suitable for application to the hair without inducing unacceptable damage. The tests may be performed with simple tensile testing apparatus without tedious examination of the hair under a microscope.

20 Claims, 7 Drawing Sheets

ASSESSMENT OF DAMAGE IN KERATIN FIBERS

BACKGROUND OF THE INVENTION

An important consideration for a hair stylist preparing to treat a person's hair, is the existing condition of the hair before the treatment commences. For example, the compositions used for applying a permanent wave for a person's hair, may be quite different for undamaged hair which has previously had no more than mild treatment, as compared with hair which has been damaged by repeated bleaching. Highly skilled operators may evaluate the existing condition of the hair and select suitable treatments based on their experience with a variety of subjective visual and tactile examinations.

Such subjective evaluations of the quality of hair and selection of hair care products suitable for application to the hair, are subject to discrepancies due to the extent of experience and skill of the operator. Because of this the optimum hair care products may not be used, and in some cases selection of too harsh a hair care treatment may result in additional damage to hair that is already damaged.

For such reasons, there has long been a desire for objective techniques for evaluating the condition of hair or for determining the level of damage of hair, so that optimum hair care products can be identified. A fairly straightforward idea has been to measure the tensile properties of individual strands of hair. When a keratin fiber such as hair is subjected to tensile force or stress, it is elongated or strained before the force becomes large enough to break the hair. Dry virgin hair (i.e, undamaged) may stretch as much as 50% before breaking.

The elongation of a keratin fiber can be represented by a conventional force-elongation curve such as illustrated in FIG. 1, which is typical for wet virgin hair. Stress or force is plotted against strain or percentage elongation. The curve, which has a rather similar shape for all keratin fibers, consists of three regions. The Hookean region, which extends up to about 5% elongation, has a relatively small amount of elongation for a given increment of force, and much of the elongation is elastic. That is, the fiber elongation is generally linear with increasing stress, and upon release of the applied stress, the fiber will largely return to its original length. Through the yield region, which extends from about 5% to 30% elongation, there is appreciable elongation for a given increment of applied stress. The post-yield region extends from about 30% elongation to the break point of the fiber. In this region the slope of the force-elongation curve again increases.

The Hookean region represents the force required to overcome coulombic interactions between the side chains of the microfibrillar proteins, and width of the region, and the shape of the curve are affected by moisture content of the fiber, pH and temperature.

The yield region of the force-elongation curve is also quite sensitive to humidity and is associated with the transformation of the alpha helical segments of the microfibrillars into beta-sheets.

Beyond 30% elongation the fiber stiffens and considerably more force must be applied to complete the alpha-beta transformation and to overcome covalent keratin bonds, which are ruptured, leading to breakage of the fiber.

Analysis of the load-elongation or stress-strain curve from a tensile test of fibers, mainly in the yield region, has been the method of choice for assessing damage to keratin fibers. Over the years, several parameters derived from the curve, have been employed, with the 20% index being the most commonly used. This index is a ratio of the work required to elongate the fiber by 20% of its original length, after the fiber has been damaged to the work required to elongate the fiber by 20% before damage. Other investigators have used a 15% index or a 30% index. Any point falling within the yield region may be selected as an index. The advantage of using an index in the yield region, is that the force is relatively constant. Therefore, moderate differences in measurements of fiber elongation do not result in significant variations in the measured force.

A disadvantage of any of these indexes, however, is the force at any point on the force-elongation curve is directly proportional to the diameter of the fiber. Oriental hair, being coarser requires more force to stretch it, than does caucasian or negroid hair. Keratin fibers vary greatly in diameter even when taken from a single source. Human hair diameter can vary by as much as 100% on the same head.

Researchers have therefore resorted to either of two tedious techniques to overcome the diameter related variability of their selected index.

Some investigators test the same fiber before and after treatment. This is accomplished by stretching the fiber in water before treatment to the desired elongation, and then allowing that fiber to relax back to near the original condition. The assumption has been that the stretching does not affect the tensile properties of the fiber significantly. The relaxation process usually requires 24 hours, after which the fiber is treated (e.g., permed, bleached, straightened or dyed) and then retested. Despite the reliability of the technique, the time consuming relaxation process makes the technique inefficient and rather unappealing.

The other technique employed to overcome diameter effects is to test fibers of comparative diameter. This necessitates the aid of a microscope to scan fibers for homogeneity along the tested length and to sort the fibers according to size. This technique can be stressful to the investigator, inefficient when large numbers of samples are to be analyzed, and require additional costly equipment. Thus, even in a laboratory setting there is a great need for a simple fast technique, utilizing the properties of the force-elongation curve independently of fiber diameter and humidity.

The stress-strain curve techniques mentioned may be suitable for a laboratory environment where "before and after" testing is conducted. This is not of direct assistance to a salon operator who wishes to evaluate preexisting hair conditions before adopting a course of treatment. A before and after type evaluation is inapplicable. Even so, some measure of hair quality may be obtained by such an index, since the stress required for a given elongation of the hair tends to be reduced by damage to the internal structure of the hair. Salon operators may use a tensile testing machine and microscope to measure hair diameter and strength for evaluating a client's hair condition. Not only is such equipment costly, the time required for reliable testing is a precious commodity and few operators perform such objective testing.

Thus, there remains a desire for a simple and fast technique for evaluating hair damage in the context of a salon, so that the hair stylist may, before treatment commences, select the desired hair care product for a given client. Preferably, the technique is independent of other properties of the hair such as diameter, which is a tedious measurement. It is also desirable that the technique be independent of humidity which can have an appreciable effect on strength properties of hair.

There are other keratin fibers where a fast, simple and reliable test for condition of the fibers is useful. For example, buyers and users of wool presently evaluate quality by subjective visual and tactile factors. It is desirable to provide objective measures of wool quality which can be used by skilled or relatively unskilled persons with reliability.

SUMMARY OF THE INVENTION

There is, therefore, provided in practice of this invention according to a presently preferred embodiment, a method for evaluating the condition of a keratin fiber by measuring the force required to elongate the fiber by a first percentage of its length, measuring the force required to elongate the fiber by a second percentage of its length, and determining the ratio between these two forces. It has been discovered that this represents a constant intrinsic property of virgin keratin fibers independent of fiber diameter, and surprisingly, independent of the source of the fiber. Further, it is found that as the force ratio increasingly deviates from the force ratio for virgin fibers, it indicates increasing damage to the internal protein structure of the fiber.

Preferably, the ratio of forces required for obtaining the given two values of elongation are determined for a hair which has been wetted sufficiently to substantially neutralize interactions other than breaking cystine bonds.

The technique may be performed with an apparatus which applies an elongating force to a keratin fiber and has means for determining the ratio of forces required to obtain each of two selected values of elongation of the fiber in the yield region of the force-elongation curve. Means are provided for displaying the force ratio or for storing a plurality of force ratios obtained by testing several fibers and displaying an average of a number of stored ratios. Such apparatus may include means for identifying a hair care product suitable for application to the tested hair, as a function of the force ratio.

BRIEF DESCRIPTION OF THE DRAWINGS

These and other features and advantages of the present invention will be appreciated as the same becomes better understood by reference to the following detailed description when .considered in connection with the accompanying drawing wherein.

DETAILED DESCRIPTION

It has been discovered that if an untreated keratin fiber is stretched under appropriate conditions the ratio of the forces of any two elongation values in the yield region of the force-elongation curve is constant, regardless of fiber diameter or source. The principal condition is that the hair is wetted to avoid effects of humidity and interfering strengthening factors. Load should also be applied to the hair at a constant rate of elongation to eliminate a possible variable.

The ratio of forces at any two elongation values therefore represents a constant intrinsic property of virgin keratin fibers. It also represents a dimensionless parameter, referred to herein as a damage index, which has been found to be diagnostic of the internal structural integrity of the fiber. Damage to the cystine bonds of the hair results in a measurable change in the force ratio or damage index which can be correlated with the subjective condition of a person's hair.

A typical procedure is to soak a strand of hair in buffered, slightly alkaline water for five minutes. The wet hair is then positioned between the grips of a tensile testing apparatus with a selected gauge length, one inch (25 mm), for example. Suitable tensile testers are described and illustrated in U.S. Pat. Nos. 3,921,443, 4,061,022 and 4,628,742. Alternatively, an Instron tensile tester Model No. 1122 equipped with a 500 gram tension load cell and data recorder may be used. A variety of other tensile testing devices on the market may also be used.

The hair is stretched at a constant rate, for example one inch (25 mm) per minute, through the yield region of the force-elongation curve. The force required to obtain a given elongation is recorded for each of two elongations within the yield region. For purposes of determining a damage index, determining the force required to obtain 10% elongation and the force required to obtain 20% elongation are convenient. There is no need for tedious examination of the hair under a microscope since the technique is independent from hair diameter, as shown below Although any two elongations within the yield region of the force-elongation curve are acceptable, the force $F_{10}$ at 10% strain and the force $F_{20}$ at 20% strain have been found to be desirable. A strain of 10% is clearly above the Hookean region of the force-elongation curve. An elongation of 20% is clearly in the yield region of the hair, even in cases of severe damage. When the forces $F_{10}$ and $F_{20}$ at two points on the force-elongation curve have been determined, the force ratio $F_{20}/F_{10}$ is calculated. Preferably the test is repeated with from five to ten different fibers, with the force ratio calculated for each fiber. The average of the separate force ratios is calculated to provide a damage index.

Figure 1:
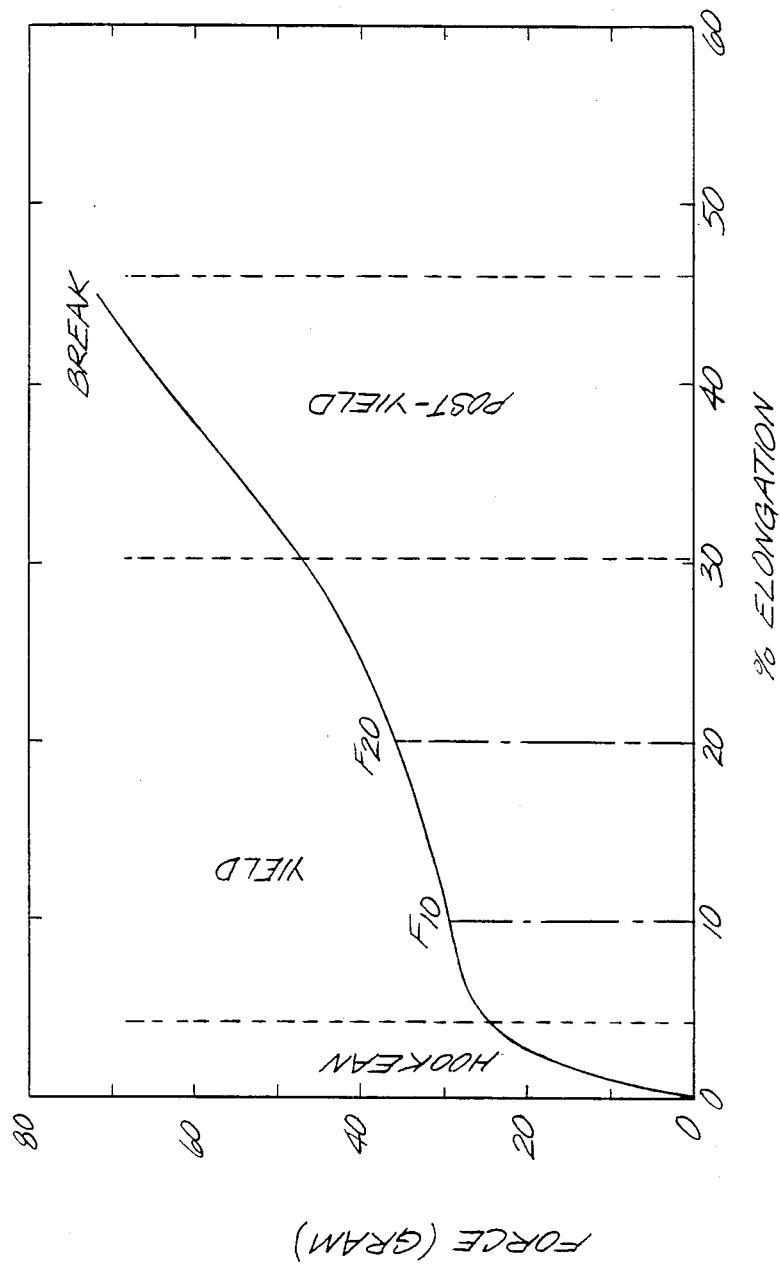
FIG. 1 is a typical force-elongation curve for a wet virgin hair.
Figure 2:
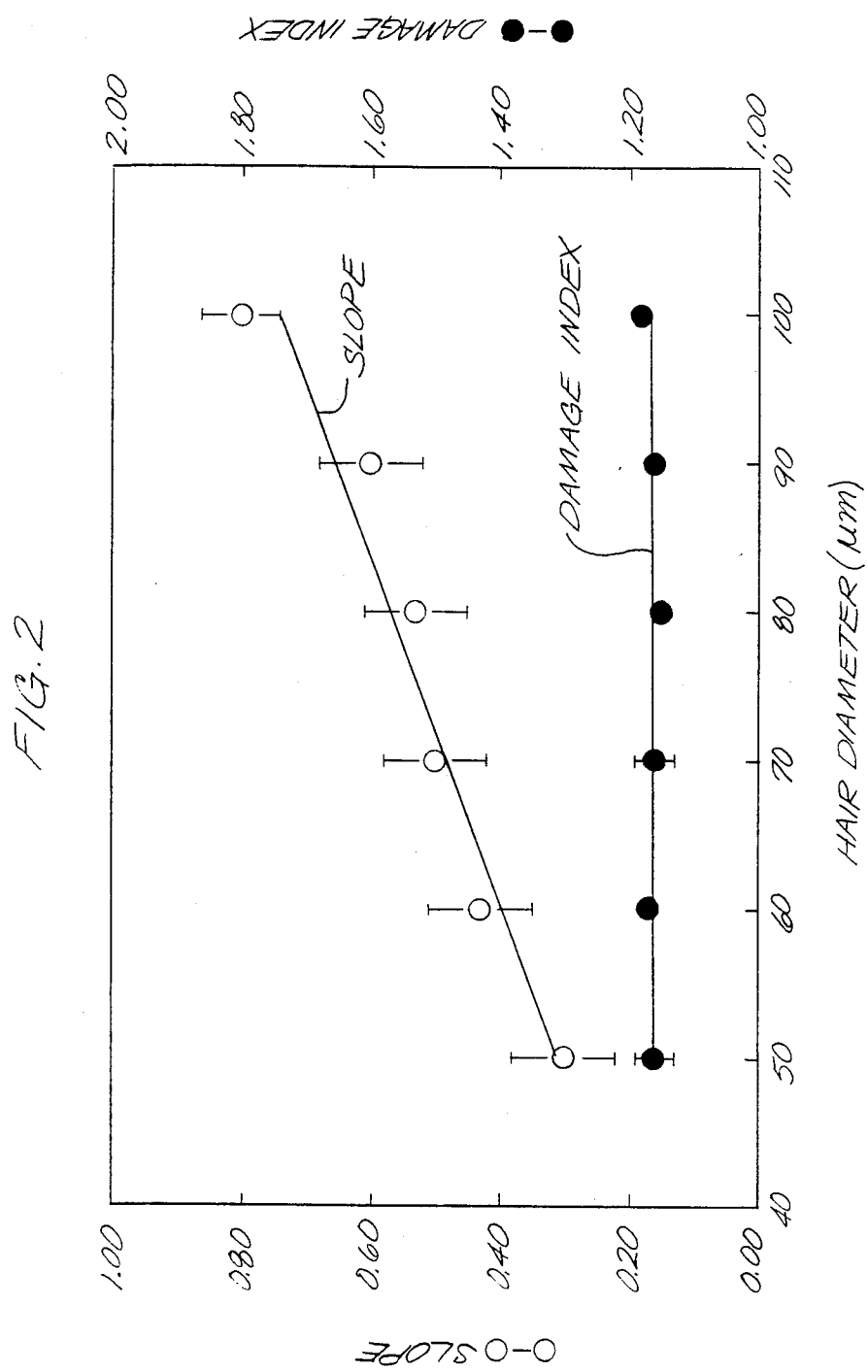
FIG. 2 is a graph illustrating both the slope of the force-elongation curve in the yield region and the novel force ratio as a function of hair diameter.

Surprisingly, for wet undamaged hair the force ratio is substantially constant regardless of the hair diameter or the source of the hair. The lower curve in FIG. 2 illustrates the force ratio $F_{20}/F_{10}$ or damage index as a function of hair diameter from 50 to 100 micrometers. As can be seen the damage index is substantially constant.

It should be noted that the force ratio is not the slope of the force-elongation curve in the yield region. The slope of the force-elongation curve varies with hair diameter as can be seen from the upper curve in FIG. 2.

Figure 3:
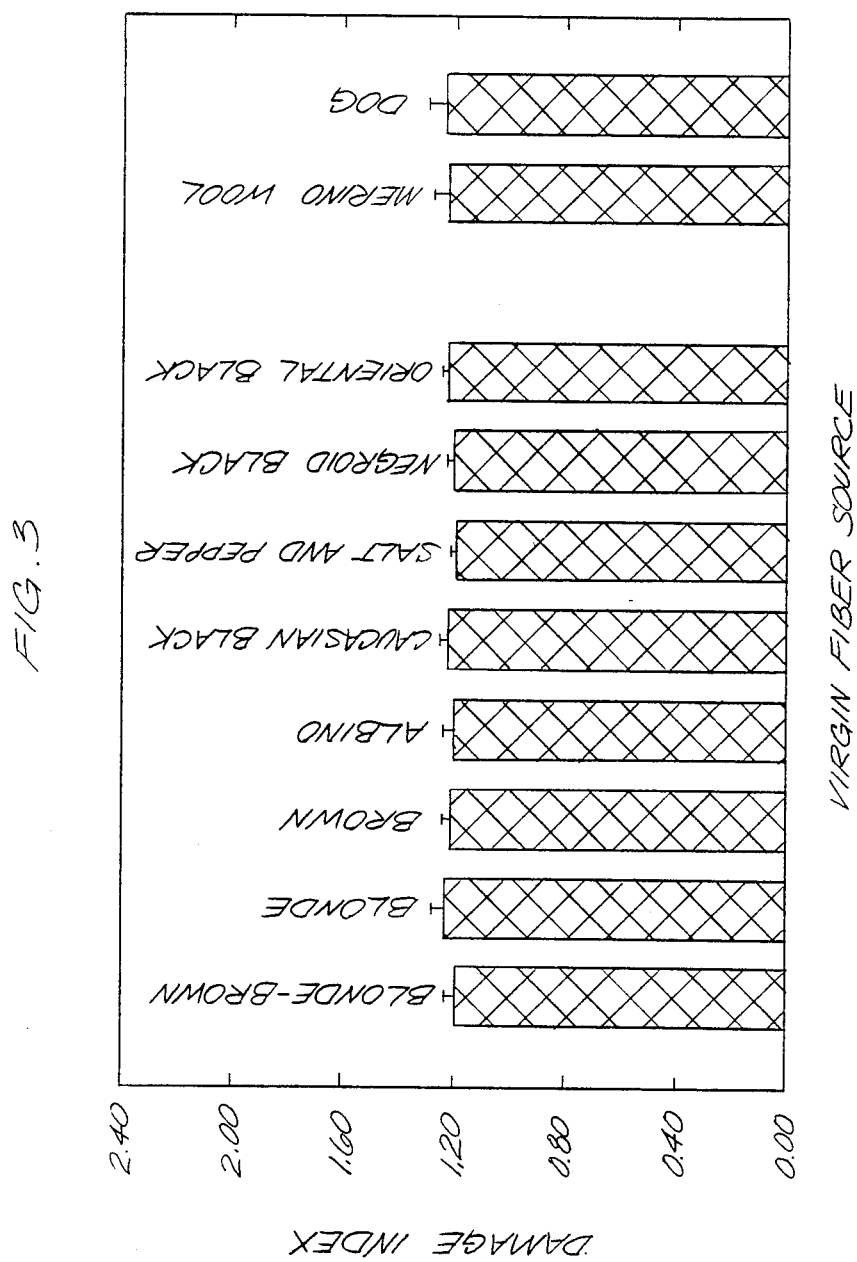
FIG. 3 is a bar chart illustrating consistency of the force ratio as a function of the source of the keratin fibers tested.

It is also found that the force ratio is substantially independent of the source of the keratin fiber. It is not only independent of the ethnic background for human hair, but also for the limited testing done, is independent of the species. FIG. 3 illustrates that the damage index or force ratio is substantially the same for oriental black hair, negroid hair, blond caucasian hair and albino hair, as well as wool from a Merino sheep or a German Shepard dog. For undamaged wet hair, the force ratio $F_{20}/F_{10}$ is $1.22 \pm 0.03$.

The force ratio may be used as a damage index for virgin and chemically treated hair. The following table indicates the force ratio or damage index for an exemplary sample of hair untreated and given treatments that damage the inherent internal protein structure of the hair. The force ratio or damage index increases significantly in proportion with damage done to the hair.

| HAIR TYPE | $F_{20}/F_{10}$ INDEX |
|---|---|
| Normal brown hair | 1.22 |
| Bleached once | 1.27 |
| Bleached twice | 1.49 |
| Heavily permed | 1.51 |
| Excessively permed | 1.66 |

The damage index has been tested on hair samples from 224 volunteers representing a large cross-section of possible hair types and hair damage. The spread in the damage index values were from 1.20 at the undamaged end of the scale to 1.72, which represents severely damaged hair. In laboratory tests, damage indexes as high as 2.20 have been obtained by bleaching permed hair two times at 40° C. Such an extreme damage index is considerably higher than that for damage encountered in routine hair treatments. At damage index values of more than about 1.9 the hair is usually so severely damaged that the majority of hair fibers break before reaching the selected 20% elongation value.

Figure 4:
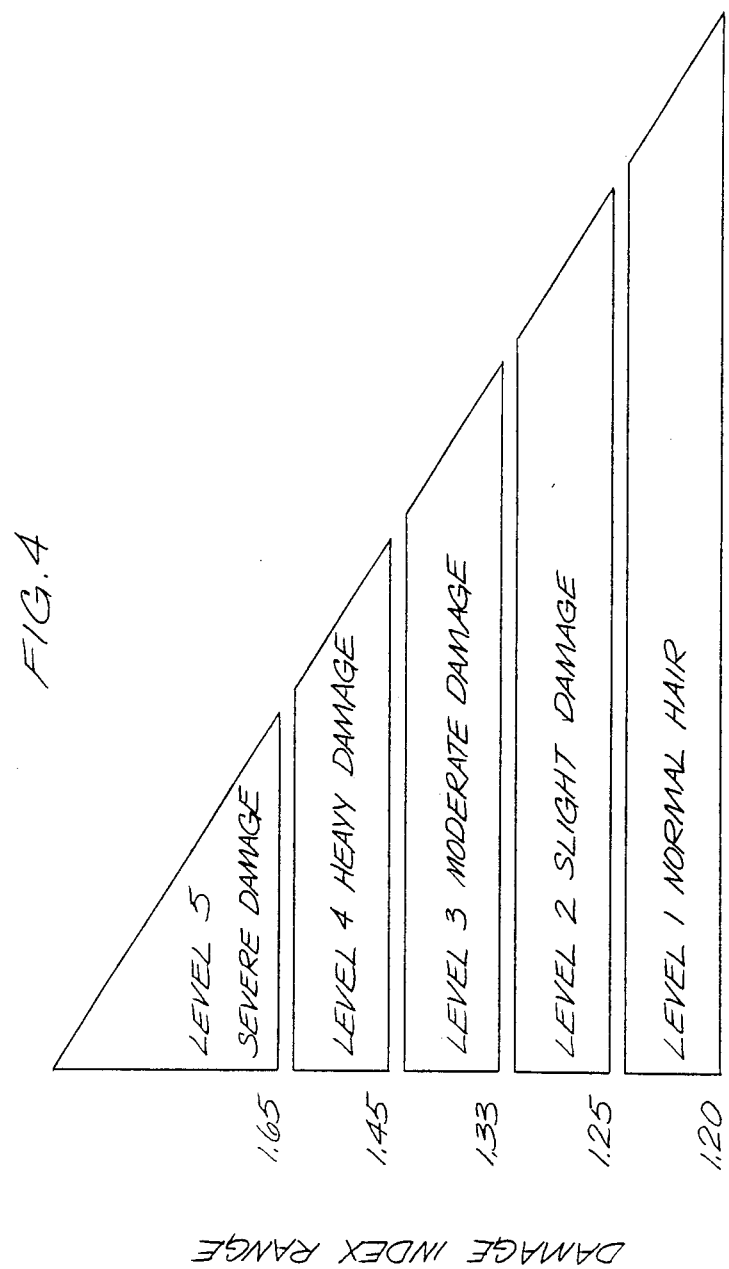
FIG. 4 is a schematic illustration of the subjective hair condition as a function of the value of the force ratio or damage index.

FIG. 4 is a chart indicating a subjective assessment of hair damage as a function of the objectively measured damage index. Thus, an inexperienced hair stylist can perform simple tensile tests on samples of a customer's hair and determine a damage index indicative of the subjective condition of the hair.

An important utility of the damage index is this diagnostic capability. Accurate assessment of the integrity of the keratin proteins of hair is vital for reducing the risk of chemically overprocessing the hair and causing damage. This particularly is important in the salon environment where the previous history of treatment of the hair may not be known, and unfortunate results may be avoided.

Figure 5:
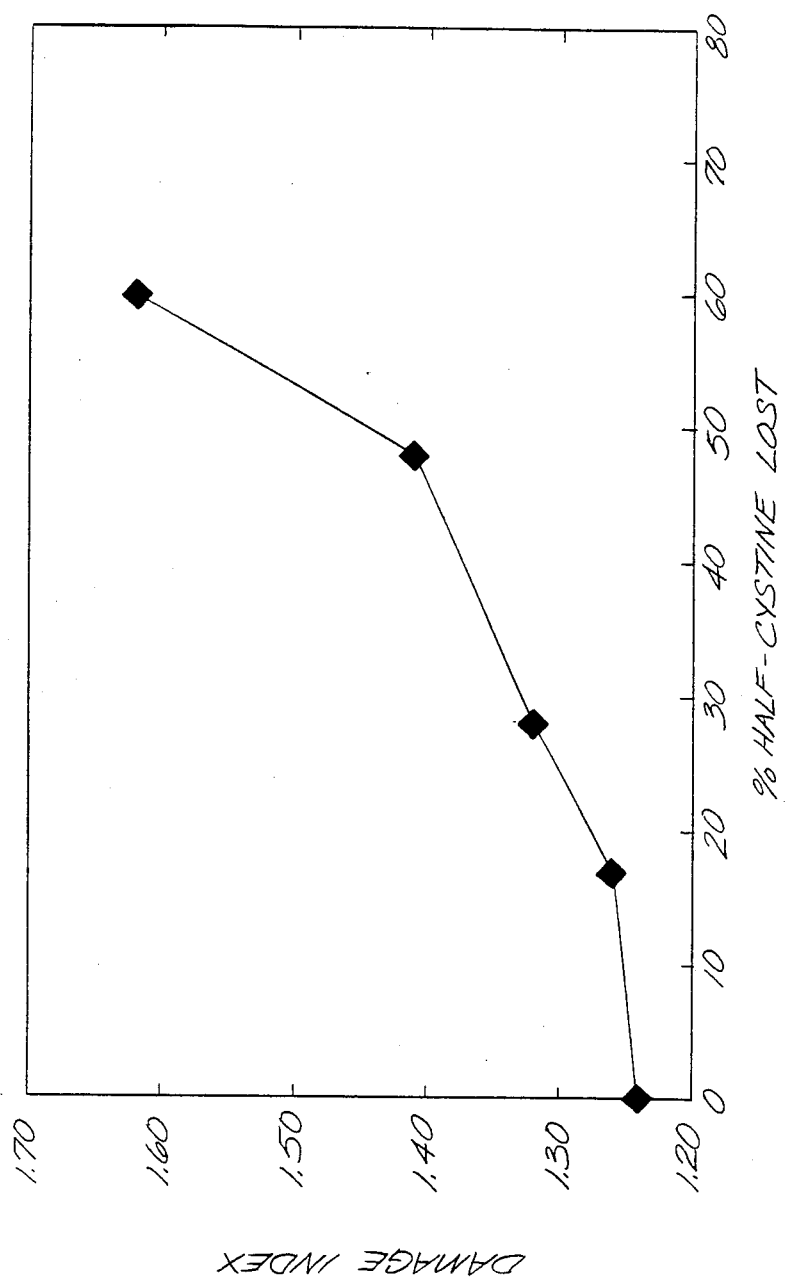
FIG. 5 is a graph illustrating the force ratio or damage index as a function of an objective analysis of hair condition.

It has also been shown that the damage index actually diagnoses the internal condition of the keratin protein. A typical virgin keratin fiber has about 16% cysteine molecules involved in disulfide bonds. Chemical treatment of the hair may irreversibly break some of the sulphur bonds, yielding two derivitives of cysteine molecules. A principal portion of the strength of the hair is damaged as the cystine bonds are broken. Perming the hair involves temporary breaking of the cystine bonds, styling the hair, and restoring most of the cystine bonds. Excessive perming with strong solutions or too long an exposure to the solution, or repeated bleaching can irreversibly damage the cystine bonding. The amount of irreversible degradation of cystine bonds was measured in hair samples and correlated with the damage index. FIG. 5 illustrates the damage index as a function of the irreversible disulfide degradation.

The tensile tests are performed on hair that has been wetted. For wetting the hair a preferred but not necessary method involves soaking the hair for two minutes or more in tap water or buffered alkaline solution up to about pH 8.5. Non-covalent amino acid side chain interactions are highly sensitive to moisture content. By pre-wetting the hair the influence of such ionic and hydrogen bonds is largely eliminated and the main resistance to elongation comes from helical transformation and covalent bonding.

Figure 6:
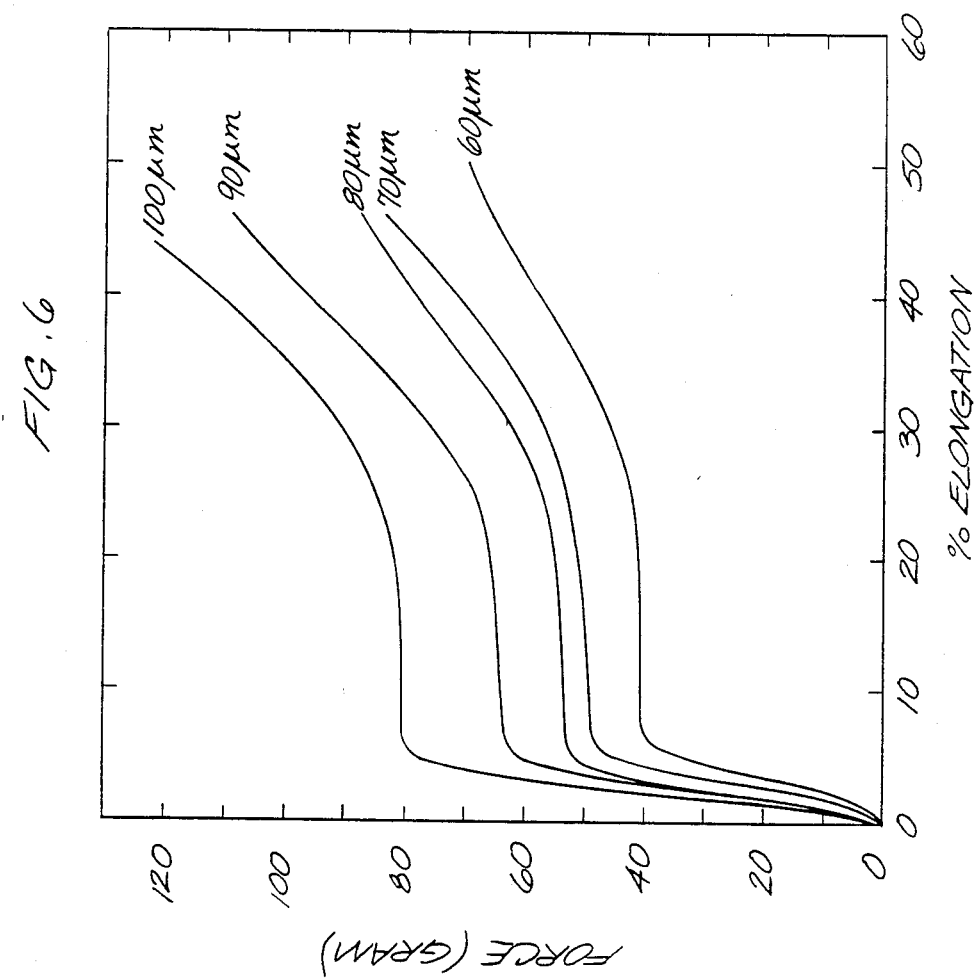
FIG. 6 is a force-elongation graph for several diameters of dry virgin hair.

FIG. 6 illustrates exemplary force-elongation curves for several diameters of dry virgin hair. As can be seen, the slope of the curve is substantially zero between 10% and 20% elongation. Thus, a force ratio for virgin dry hair is about 1.0. Further, it is found that the force ratio remains about 1.0 regardless of damage to the inherent disulfide cystine bonds of the keratin fiber. The ionic and hydrogen bonds are quite sensitive to humidity and the resultant variability may mask inherent properties one desires to measure. For example, bleached hair can be enriched in ionic bonding and that strength in dry hair can mask measurement of the inherent disulfide bond strength remaining in the hair. Thus, it is considered significant to perform the tensile tests and determine the damage index on wet hair. Testing of wet hair indicates the status of the disulfide bonds affected during permanent waving of the hair.

One may simply use a chart recorder or X-Y plotter for plotting a force-elongation curve. One can then manually measure the forces at selected elongations and calculate the force ratio. It is preferable, however, to provide automatic equipment which can be easily operated by an inexperienced hairstylist in a salon environment. Such equipment may also be used for automatically identifying exemplary hair care products suitable for treatment of hair as a function of the damage index.

Figure 7:
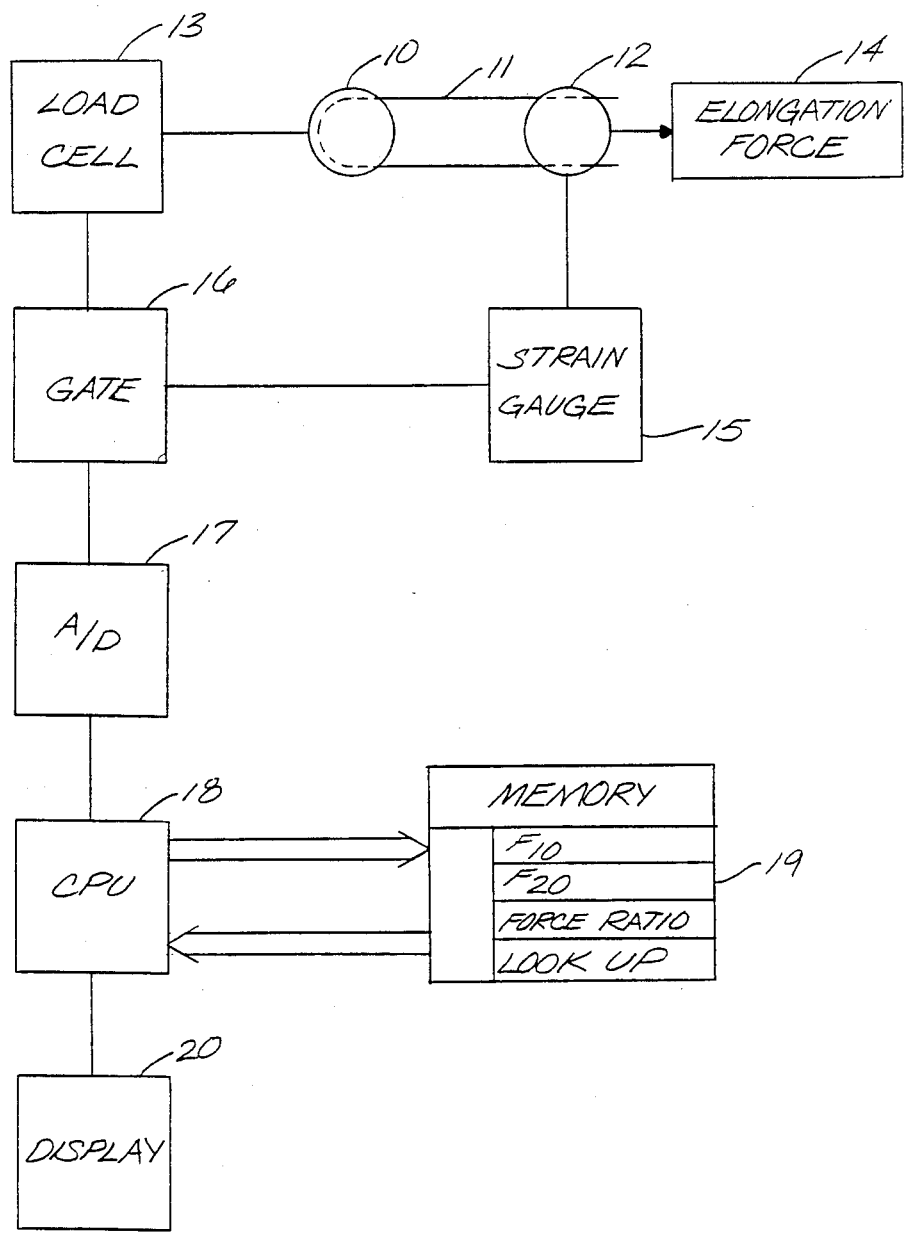
FIG. 7 illustrates in block form an apparatus for evaluating hair condition using the novel damage index.

FIG. 7 illustrates in block diagram form suitable apparatus. Exemplary apparatus may be similar to that described in the aforementioned U.S patents. Such apparatus comprises a cylindrical post 10 with a groove around which the middle of a strand of hair 11 is wrapped. The ends of the strand of hair are clamped between two parts of an adjacent grip 12, which may grip the hair by pneumatic or spring action. The substantially fixed post 10 is connected to a conventional load cell 13 for measuring the tensile load on the strand of hair. Means 14 are provided for applying an elongation force for moving the grip 12 away from the fixed post and thereby elongating the strand of hair. The elongation force may be applied at a constant rate by a screw, cam or hydraulic actuator.

The grip is connected to a strain measuring gauge 15 for determining the elongation of the strand of hair. A gate 16 permits reading of the load cell for measuring the force applied to the hair when the strain gauge records a selected elongation, such as 10% and 20%. These two forces $F_{10}$ and $F_{20}$ are converted to digital values by an analog to digital converter 17 and fed to a digital central processing unit 18. The two forces $F_{10}$ and $F_{20}$ are temporarily stored in a memory 19. The CPU also calculates a force ratio $F_{20}/F_{10}$ or damage index for each fiber tested, and the resultant ratios are also stored in the memory.

When a number of fibers have been tested the operator causes the CPU to calculate an average of the stored ratios for the fibers and the average is shown on a display 20. The operator may also select a certain desired treatment, such as a permanent wave, and key that treatment into the CPU. The apparatus then searches a look up table in the memory for identifying a permanent wave lotion, or the like, suitable for application to hair with the measured damage index. The identified product or products are also displayed or may be provided in the form of a personalized printout of hair care products suitable for the hair of the individual tested.

Although described in one embodiment, it will be apparent that the invention may be practiced otherwise than specifically described. In the examples given it is assumed that testing is in a salon environment for evaluating the condition of a customer's hair before treatment. It will also be apparent that such a technique is of considerable value for research and for evaluation of existing or proposed hair treatment compositions or regimen, to determine the extent of damage of the disulfide hair bonds that occurs by reason of such treatment. It will also be apparent that this invention is also suitable for testing the quality of wool or other keratin fibers which are presently largely judged on a subjective basis.

The preferred force ratio $F_{20}/F_{10}$ may be varied as desired for a particular purpose. Thus, a different force ratio may be appropriate for testing wool or for evaluating experimental compositions to obtain a different sensitivity than appropriate for determining hair damage in a salon environment.

It is, therefore, to be understood that the scope of this invention is defined by the following claims.

What is claimed is:

1. A method for analyzing keratin fiber comprising the steps of:
   measuring a first force required to obtain a first value of elongation of a keratin fiber in the yield region of the force-elongation curve of the keratin fiber;
   measuring a second force required to obtain a second, relatively higher value of elongation of a keratin fiber in the yield region of the force-elongation curve; and
   determining the ratio of the second force and the first force.

2. A method as recited in claim 1 comprising the preliminary step of wetting the keratin fiber before measuring the forces.

3. A method as recited in claim comprising measuring the force ratio for a plurality of keratin fibers and determining an average force ratio.

4. A method as recited in claim 1 further comprising displaying a hair care product recommendation which is a function of the force ratio.

5. A method as recited in claim 1 further comprising selecting a hair care product suitable for the keratin fiber as a function of the force ratio.

6. A method for evaluating the condition of hair comprising the steps of:
   measuring the force required to elongate a strand of hair a first percentage of its length;
   measuring the force required to elongate the strand of hair a second percentage of its length; and
   determining a ratio between the first and second forces.

7. A method as recited in claim 6 comprising the preliminary step of wetting the strand of hair before elongation.

8. A method as recited in claim 6 further comprising comparing the determined force ratio with a known correlation of force ratio as a function of keratin damage.

9. A method as recited in claim 6 further comprising selecting a hair care product suitable for the hair as a function of the force ratio.

10. A method as recited in claim 6 comprising measuring a plurality of strands of hair from the same source, determining a force ratio for each of the strands of hair, and determining an average of the force ratios.

11. A method as recited in claim 6 comprising wetting the hair sufficiently to substantially eliminate noncovalent amino acid side-chain interactions.

12. A method as recited in claim 6 wherein the first and second percentages lie in the yield region of the force-elongation curve of the strand.

13. Apparatus for assessing condition of a keratin fiber comprising:
   means for applying an elongating force to a keratin fiber;
   means connected to the means for applying force for determining a ratio of forces required to obtain a selected two values of elongation of the keratin fiber in the yield region of the force-elongation curve for the keratin fiber; and
   means connected to the means for determining a ratio for displaying the force ratio.

14. Apparatus as recited in claim 13 wherein the means for displaying comprises means for displaying a damage index which is a function of the force ratio.

15. Apparatus as recited in claim 13 wherein the means for displaying comprises means for displaying a hair care product recommendation which is a function of the force ratio.

16. Apparatus as recited in claim 13 further comprising means for storing a plurality of force ratios for a plurality of tests of keratin fibers and means for determining an average force ratio for the plurality of tests.

17. Apparatus for evaluating condition of hair comprising:
   means for elongating a strand of hair;
   means connected to the means for elongating for measuring force applied to the hair at first and second selected elongations;
   means connected to the means for measuring for determining the ratio of the first and second forces; and
   means connected to the means for determining the ratio for displaying the ratio of forces.

18. Apparatus as recited in claim 17 further comprising means for storing a plurality of force ratios for a plurality of tests of strands of hair and means for determining an average force ratio for the plurality of tests.

19. Apparatus as recited in claim 17 wherein the means for displaying comprises means for displaying a hair care product recommendation which is a function of the force ratio.

20. Apparatus as recited in claim 17 wherein the means for displaying comprises means for displaying a damage index which is a function of the force ratio.

* * * * *

UNITED STATES PATENT AND TRADEMARK OFFICE
CERTIFICATE OF CORRECTION

PATENT NO.   : 4,972,718
DATED        : November 27, 1990
INVENTOR(S)  : Hayel M. Said; Leroy D. Hunter; Roger A. Mathews It is certified that error appears in the above-identified patent and that said Letters Patent is hereby corrected as shown below:

Column 4, line 45, after "below" insert a period.

Column 7, line 52, after "claim" insert -- 1 --.

Signed and Sealed this

Twenty-eighth Day of April, 1992

Attest:

HARRY F. MANBECK, JR.

*Attesting Officer*     *Commissioner of Patents and Trademarks*